(12) United States Patent
De Meuter et al.

(10) Patent No.: US 7,781,009 B2
(45) Date of Patent: Aug. 24, 2010

(54) SUGAR-FREE HARD COATINGS PREPARED FROM LIQUID MALTITOL COMPRISING $DP_{4+}$ FRACTION

(75) Inventors: Pascale Adolphine Emilienne De Meuter, Vilvoorde (BE); Michel Henri André Gonze, Brussels (BE); Robert Henri-Marcel Stouffs, Ferrara (IT)

(73) Assignee: Cerestar Holding B.V., La Sas Van Gent (NL)

( * ) Notice: Subject to any disclaimer, the term of this patent is extended or adjusted under 35 U.S.C. 154(b) by 709 days.

(21) Appl. No.: 10/509,835

(22) PCT Filed: Apr. 25, 2003

(86) PCT No.: PCT/EP03/04354

§ 371 (c)(1),
(2), (4) Date: Sep. 30, 2004

(87) PCT Pub. No.: WO03/092400

PCT Pub. Date: Nov. 13, 2003

(65) Prior Publication Data

US 2005/0214424 A1    Sep. 29, 2005

(30) Foreign Application Priority Data

Apr. 27, 2002    (GB) ................. 0209671.7

(51) Int. Cl.
A23G 3/00    (2006.01)

(52) U.S. Cl. ............................ 426/660; 426/5; 426/103

(58) Field of Classification Search .................... 426/5, 426/660

See application file for complete search history.

(56) References Cited

U.S. PATENT DOCUMENTS

| 4,840,797 | A | * | 6/1989 | Boursier ..................... 424/475 |
| 4,849,023 | A | * | 7/1989 | Devos et al. ................... 127/40 |
| 5,470,591 | A | * | 11/1995 | Ribadeau-Dumas et al. ... 426/3 |
| 5,478,593 | A | | 12/1995 | Serpelloni et al. |
| 5,527,542 | A | | 6/1996 | Serpelloni et al. |
| 5,571,547 | A | | 11/1996 | Serpelloni et al. |
| 5,665,406 | A | | 9/1997 | Reed et al. |
| 6,558,722 | B2 | * | 5/2003 | Corriveau et al. ........... 426/293 |

FOREIGN PATENT DOCUMENTS

| EP | 0 201 412 A | 11/1986 |
| JP | 61-263915 | 11/1986 |
| JP | S61-263915 A1 | 11/1986 |
| JP | 2002-017266 A1 | 1/2002 |
| WO | WO 91/09989 | 7/1991 |

\* cited by examiner

*Primary Examiner*—Keith Hendricks
*Assistant Examiner*—Nikki H Dees

(57) ABSTRACT

The present invention discloses a sugar-free hard coating prepared from a liquid maltitol syrup comprising $DP_{4+}$ fraction. In the chewing gum process, the liquid maltitol can be applied at high dry substance, i.e. higher than 65%. The obtained hard coating is crunchy, non-sticky and is not cracking during post-processing.

12 Claims, 1 Drawing Sheet

SUGAR-FREE HARD COATINGS PREPARED FROM LIQUID MALTITOL COMPRISING $DP_{4+}$ FRACTION

This application is the U.S. National phase filing of PCT/EP03/04354, filed Apr. 25, 2003, the complete disclosure of which is incorporated herein by reference, and which was published under PCT Article 21(2) in English.

TECHNICAL FIELD

The present invention relates to a sugar-free hard coating prepared from a liquid coating syrup of maltitol comprising $DP_{4+}$ fraction and from 95 and 97% maltitol by weight of the dry matter content. The present invention relates to sugar-free hard-coated comestibles having regular surfaces and non-sticky hard coating.

BACKGROUND OF THE INVENTION

Conventional panning procedures to prepare hard coatings generally work with sucrose, but recent advances in panning have allowed the use of other carbohydrate materials to be used in the place of sucrose. Sucrose proves to be detrimental for teeth and causes dental caries due to easy formation of acids. Therefore coatings are nowadays increasingly made of sugar-free compositions.

The appearance of the coating is sometimes affected by the crystallisation difficulties. To obtain good hard coatings, even crystallisation must occur during application and drying.

EP 0 201 412 describes a confectionery or pharmaceutical product provided with a hard sugarless coating obtained by hard coating using a maltitol syrup having a dry matter content from 50 to 70% by weight, the said coating being essentially crystalline and comprising at least 90% by weight of maltitol.

SUMMARY OF THE INVENTION

The present invention relates to sugar-free hard-coated comestibles consisting of a hard coating and an edible, chewable and/or pharmaceutical core and said hard coating is obtainable by using a coating syrup comprising at least 95% maltitol and characterised in that dry matter content of syrup is from 68-72%, and dry matter content of syrup is comprising from 0.7-1.5% by weight of $DP_{4+}$.

The present invention relates to sugar-free hard-coated comestibles wherein the hard coating is obtainable from a maltitol syrup which is consisting of:
a) From 95-97% by weight of maltitol,
b) Maximum 1.5% by weight of $DP_1$,
c) From 0-1.5% by weight of $DP_3$, and
d) From 0.7-1.5% by weight of $DP_{4+}$.

The current invention further relates to sugar-free hard-coated comestibles wherein the core is selected from the group consisting of pharmaceutical tablets, chewing gum, confectionery product, chocolate and nut.

The current invention describes a sugar-free hard-coated comestible wherein the core is chewing gum and the hard coating is non-sticky and the surface of the hard coating is regularly formed and remains intact during processing.

The current invention relates to a process for preparing sugar-free hard-coated comestibles and said process is comprising the following steps:
a) Applying a coating syrup, which is containing a maltitol syrup, onto the cores of the comestibles in a moving bed of a coating apparatus,
b) Applying maltitol in powder form for obtaining coated cores.
c) Drying the coated cores by using drying air in the temperature range of from 15 to 45° C. and a moisture content of at most 50% relative humidity and said process is characterised in that maltitol syrups of step a) has a dry matter content from 68-72% and said maltitol syrup is comprising 0.7-1.5% by weight of $DP_{4+}$.

The current invention relates to a process wherein in step a) dry matter content of maltitol syrup is consisting of:
i) From 95-97% by weight of maltitol,
ii) Maximum 1.5% by weight of DP1,
iii) From 0-1.5% by weight of DP3,
iv) From 0.7-1.5% by weight of $DP_{4+}$.

Furthermore, the current invention relates to the use of maltitol syrup comprising from 0.7-1.5% $DP_{4+}$ on dry matter for improving hard coating of hard-coated comestibles.

The current invention relates to said use wherein the syrup has a dry matter content of from 68-72%.

Figure 1:
FIG. 1 is a photograph, with magnification of 6×10.

It shows that the hard coating prepared with the liquid maltitol syrup of 96% maltitol and 0.7-1.5% by weight of $DP_{4+}$ based on dry matter, is giving a smooth regular surface.

DETAILED DESCRIPTION OF THE INVENTION

The present invention relates to sugar-free hard-coated comestibles consisting of a hard coating and an edible, chewable and/or pharmaceutical core and said hard coating is obtainable by using a coating syrup comprising at least 95% maltitol and characterised in that dry matter content of syrup is from 68-72%, and dry matter content of syrup is comprising from 0.7-1.5% by weight of $DP_{4+}$.

The present invention relates to sugar-free hard-coated comestibles wherein the hard coating is obtainable from a maltitol syrup which is consisting of:
a) From 95-97% by weight of maltitol,
b) Maximum 1.5% by weight of $DP_1$,
c) From 0-1.5% by weight of $DP_3$, and
d) From 0.7-1.5% by weight of $DP_{4+}$.

EP 0 201 412 describes a maltitol syrup which is consisting of 97.1% by weight of maltitol, 1.1% by weight of sorbitol and 1.8% by weight of maltotriitol. Said syrup is devoid of any $DP_{4+}$ fraction and it is clearly demonstrated that it is not possible to obtain a regular surface when applying the maltitol syrup at a dry substance content higher than 65%. In cases where higher dry substance is used, the crystallisation is irregular and defects on the surface appear.

Surprisingly, the current invention demonstrates that maltitol syrups containing from 0.7-1.5% $DP_{4+}$ on dry matter content, and from 95-97% maltitol on dry matter content, are suitable to use syrups at a dry substance higher than 65%, i.e. at dry substance of 68-72% and yet regular hard coatings are obtained (see FIG. 1). Preferably, maltitol syrups having a dry matter content from 70-72%, result in a hard coating with a homogeneous surface.

The hard coatings can be prepared according to a process which is similar to the process described for sorbitol coating in WO 91/09989, and said hard coating process comprises the following steps:
a) Applying a coating syrup, containing maltitol syrup, onto the cores of the comestibles in a moving bed of a coating apparatus, b) Applying maltitol in powder form for obtaining coated cores, c) Drying the coated cores by using drying air in the temperature range of from 15 to 45° C. and a moisture content of at most 50% relative humidity and said process is characterised in that maltitol syrup of step a) has a dry matter content from 68-72% and said maltitol syrup is comprising 0.7-1.5% by weight of $DP_{4+}$.

The current invention relates to a process wherein step a) dry matter is content of maltitol syrup is consisting of:
i) From 95-97% by weight of maltitol,
ii) Maximum 1.5% by weight of DP1,
iii) From 0-1.5% by weight of DP3,
iv) From 0.7-1.5% by weight of $DP_{4+}$.

The hard coating can be prepared by applying a coating syrup which is containing besides the maltitol syrup, additives, such as anti-sticking components, binding agents, dispersing agents, film formers, colourings agents and/or flavouring agents. In fact, any colouring agent which is approved for use in foodstuffs may be used. Furthermore, flavouring agents in liquid or solid form of both natural and synthetic origin can be used.

The hard coating of said sugar-free hard-coated comestibles consists of from 1 to 100 layers.

In general a plurality of layers is obtained by applying single coats allowing the layers to dry, and then repeating the process. Any number of the coats may be applied to the core. Coatings of from 1 to 100 layers are easily obtained, preferably the number of layers is between 1 and 40. The optimal amount of layers will depend on the desired application and can be determined experimentally.

The current invention further relates to sugar-free hard-coated comestibles wherein the core is selected from the group consisting of pharmaceutical tablets, chewing gum, confectionery product, chocolate and nut.

Especially a sugar-free hard-coated comestible wherein the core is chewing gum and the hard coating is non-sticky and the surface of the hard coating is regularly formed and remains intact during processing and during any post-treatment (such as packaging) is disclosed by the current invention. A coating syrup prepared from a maltitol syrup which is comprising 99-100% by weight of maltitol, gives a coating which is brittle and results in breakage and causes problems after processing, such as during packaging, etc.

The effectiveness of the current invention is further demonstrated by the hard coating of a chewing gum (example 1—FIG. 1). FIG. 1 demonstrates the regular surface of the hard coating.

Furthermore, the current invention relates to the use of maltitol syrup comprising from 0.7-1.5% $DP_{4+}$ on dry matter for improving hard coating of hard-coated comestibles.

The current invention relates to said use wherein the syrup has a dry matter content of from 68-72%.

The use of said maltitol syrup results in a regular surface of hard coating.

In particular the content of $DP_{4+}$ in the liquid maltitol syrup, makes the current syrup suitable for hard coating process and for obtaining a regular surface.

The current invention has the following advantages:
the liquid maltitol syrup can be applied at high dry matter content and yet regular surfaces of hard coating can be obtained,
the process for hard coating does not need evaporation of the excess of water, since the liquid maltitol syrup is available at high dry substance, and this is resulting in a more economical process.
the coating remains intact during processing and during handling afterwards, such as during packaging etc, The present invention is illustrated by way of the following example.

EXAMPLE 1

The coating was performed in a 2 kg coating pan.

1.5 kg cores, wherein the weight of uncoated centres was 0.9 g each, were rotating at 8 rpm. 5 ml coating syrup (liquid maltitol syrup consisting of 96% maltitol, 1.4% DP1, 1.4% DP3, and 0.9% DP4+ based on dry matter content and having a dry matter content of 70.3%) (C☆Maltidex 163K9) was spread over the centres. Dry maltitol powder was added to avoid stickiness and to start the crystallisation. The drying step was carried out by blowing air into the coating pan at 24° C. The coating was built up by repetitively applying this process. The amount of syrup added increased up to 30 ml/layer.

The coated chewing gum is shown in FIG. 1, wherein it is clearly demonstrated that the hard coating has a regular, homogeneous surface.

The hard coating remains intact during processing and during handling (packaging) afterwards.

The invention claimed is:

1. Sugar-free hard-coated comestibles consisting of a hard coating and an edible, chewable and/or pharmaceutical core that is elected from the group consisting of pharmaceutical tablets, chewing gum, confectionery product, chocolate and nut, and said hard coating is obtainable by using a coating syrup comprising at least 95% maltitol and characterised in that
a) dry matter content of syrup is from 68-72% and
b) dry matter content of syrup is comprising from 0.7-1.5% by weight of $DP_{4+}$.

2. Sugar-free hard-coated comestibles according to claim 1, characterised in that said maltitol syrup consists of:
a) from 95-97% by weight of maltitol,
b) a maximum of 1.5% by weight of DP1,
c) from 0-1.5% by weight of DP3,
d) from 0.7-1.5% by weight of $DP_{4+}$.

3. Process for preparing sugar-free hard-coated comestibles and said process comprising the following steps:
a) applying a coating syrup, containing a maltitol syrup, onto the cores of the comestibles in a moving bed of a coating apparatus,
b) applying maltitol in powder form for obtaining coated cores,
c) drying the coated cores by using drying air in the temperature range of from 15 to 45° C. and a moisture content of at most 50% relative humidity, and said process is characterised in that maltitol syrups of step a) has a dry matter content from 68-72% and said maltitol syrup comprises 0.7-1.5% by weight of $DP_{4+}$.

4. Process according to claim 3 characterised in that in step a) dry matter of maltitol syrup is consisting of:
a) from 95-97% by weight of maltitol,
b) a maximum of 1.5% by weight of DP1,
c) from 0-1.5% by weight of DP3,
d) from 0.7-1.5% by weight of $DP_{4+}$.

5. Sugar-free comestibles according to claim 1, characterized in that the dry matter content of said syrup is from 70-72%.

6. Sugar-free comestibles according to claim 1, characterized in that said comestibles have a smooth, regular surface.

7. Sugar-free comestibles according to any one of claims 1, 2, 5 or 6, characterised in that the core is chewing gum and the hard coating is non-sticky and the surface of the hard coating is regularly if formed and remains intact during processing.

8. Sugar-free comestibles according to claim 5, wherein said hard coating has a homogeneous surface.

9. Sugar-free comestibles according to claim 1, wherein said hard coating consists of 1 to 100 layers.

10. Sugar-free comestibles according to claim 1, wherein said maltitol syrup contains 0 to 1.5% by weight $DP_{+3}$.

11. The process according to claim 3, wherein said cores comprise chocolate.

12. The process according to claim 3, wherein said cores comprise nuts.

* * * * *